(12) United States Patent
Udartsev

(10) Patent No.: US 11,583,432 B2
(45) Date of Patent: Feb. 21, 2023

(54) DEVICE FOR DISCHARGE AND COLLECTION OF INTESTINAL GASES

(71) Applicant: Dobroslav Viktorovich Udartsev, Novosibirsk (RU)

(72) Inventor: Dobroslav Viktorovich Udartsev, Novosibirsk (RU)

( * ) Notice: Subject to any disclaimer, the term of this patent is extended or adjusted under 35 U.S.C. 154(b) by 0 days.

(21) Appl. No.: 16/646,316

(22) PCT Filed: Sep. 6, 2018

(86) PCT No.: PCT/RU2018/050105
§ 371 (c)(1),
(2) Date: Mar. 11, 2020

(87) PCT Pub. No.: WO2019/125221
PCT Pub. Date: Jun. 27, 2019

(65) Prior Publication Data
US 2020/0268544 A1    Aug. 27, 2020

(30) Foreign Application Priority Data
Dec. 22, 2017 (RU) .......................... RU2017145379

(51) Int. Cl.
*A61F 5/451* (2006.01)
*A61M 1/00* (2006.01)

(52) U.S. Cl.
CPC .............. *A61F 5/451* (2013.01); *A61M 1/84* (2021.05); *A61M 2210/1067* (2013.01)

(58) Field of Classification Search
CPC . A61F 5/451; A61M 1/84; A61M 2210/1067; A61B 10/0038; A61H 21/00; A61H 19/00
See application file for complete search history.

(56) References Cited

U.S. PATENT DOCUMENTS

| | | | |
|---|---|---|---|
| 1,947,150 A * | 2/1934 | Bacon ................. | A61M 3/0279 604/278 |
| 3,459,175 A * | 8/1969 | Miller ................ | A61M 25/0108 600/431 |
| 3,990,448 A * | 11/1976 | Mather ................ | A61M 3/0279 604/275 |

(Continued)

FOREIGN PATENT DOCUMENTS

| | | |
|---|---|---|
| AU | 2007308971 A1 | 5/2008 |
| RU | 27488 U1 | 2/2003 |

(Continued)

*Primary Examiner* — Benjamin J Klein
*Assistant Examiner* — Hans Kaliher
(74) *Attorney, Agent, or Firm* — Muncy, Geissler, Olds & Lowe, P.C.

(57) ABSTRACT

The utility model relates to rectally installed devices for intestinal gases drainage.
User comfort is improved due to the fact that the device for silent removal and collection of intestinal gases is made in the form of a hollow oblong housing with two collar projections, proximal and distal, on the outer surface of the oblong housing, between which there is a window connected in the flowing medium with the outlet; there is a stop at the outlet.
The window may consist of several inlets located circumferentially between the collar protrusions; there are drainage grooves on the outer side of the distal collar protrusion.

5 Claims, 4 Drawing Sheets

(56) References Cited

U.S. PATENT DOCUMENTS

| | | | | |
|---|---|---|---|---|
| 4,261,340 A | * | 4/1981 | Baumel | A61F 2/0009 600/32 |
| 4,419,099 A | * | 12/1983 | Miller | A61M 3/0279 604/533 |
| 4,563,182 A | * | 1/1986 | Stoy | A61F 5/0093 424/436 |
| 4,943,276 A | * | 7/1990 | Ghedina | A61F 5/00 128/DIG. 25 |
| 4,943,285 A | * | 7/1990 | Hawks | A61M 3/0279 600/29 |
| 5,921,970 A | * | 7/1999 | Vandenberg | A61M 1/84 604/275 |
| 6,221,004 B1 | * | 4/2001 | Kahl | A61F 5/451 600/29 |
| 6,902,557 B2 | * | 6/2005 | Mezzoli | A61M 3/027 604/514 |
| 7,122,025 B1 | * | 10/2006 | Nestenborg | A61F 5/451 604/540 |
| 2017/0027811 A1 | * | 2/2017 | Thomas | A61H 21/00 |

FOREIGN PATENT DOCUMENTS

| | | |
|---|---|---|
| RU | 2454976 C2 | 7/2012 |
| RU | 2014141019 A | 5/2016 |

\* cited by examiner

DEVICE FOR DISCHARGE AND COLLECTION OF INTESTINAL GASES

This nonprovisional application is a continuation of International Application No. PCT/RU2018/050105, which was filed on Sep. 6, 2018, and which claims priority to Pussian Patent Application No. 2017145379, which was filed in Russia on Dec. 22, 2017, and which are both herein incorporated by reference.

BACKGROUND OF THE INVENTION

The utility model relates to the satisfaction of human needs, in particular, to some rectally installed intestinal gas drainage devices.

The closest technical solution is the "RECTAL PROBE" RU PM 27488 [1] made in the form of a hollow oblong housing with a window on the side wall of the housing connected in the flowing medium with an outlet located at the proximal end face of the oblong housing.

The disadvantage is the low functionality due to the impossibility of constantly carrying the device. The known device can be used only in hospitals and requires the help of a specialist. Another disadvantage is that the user of the patient cannot regulate the gas venting from the rectum, which results in a decrease in their comfort and the quality of life, in particular, in dietary restrictions. The disadvantages also include an increased sound generation during flatulence, which causes discomfort to others.

The technical result of the proposed utility model is increased functionality due to increased user mobility and comfort, with, among others, removed dietary restrictions and improved comfort of others.

SUMMARY OF THE INVENTION

The technical result is achieved as follows: the device for the removal and collection of intestinal gases made in the form of a hollow oblong housing, with a window on the side wall of the housing connected in flowing medium with the outlet located at the proximal (relative to the outlet) end of the oblong housing has two collar protrusions (rims), proximal and distal, on the outer surface of the oblong housing. There is a window between the protrusions connected in the flowing medium with the outlet hole; there is a stopper at the outlet.

Each collar protrusion can be limited by two conical surfaces with adjacent bases. The distal protrusion has oval bases in section, which improves the manufacturability and allows the user to control the flatulence process.

The window may consist of several inlets located circumferentially between the collar protrusions. There are drainage grooves on the outer side of the distal collar protrusion, which facilitate the removal of gases and user adjustment of the gas takeoff by the internal tension of the anal sphincter muscles.

Inside the housing (between the window and the outlet), there may be a silencer, or a device for creating various sounds, which will further reduce the sound volume during gas emission or will give harmony. The silencer can be made, for example, as a cylindrical insert with vanes.

Inside the distal part of the housing, there may be a silencer lock with a tube for venting and/or collecting gases. The silencer lock may also be simultaneously the tube holder and, for example, may be manufactured in the form of a split sleeve with an outer flange that is inserted into the groove of the silencer lock in the housing and an inner flange holding the vent tube.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
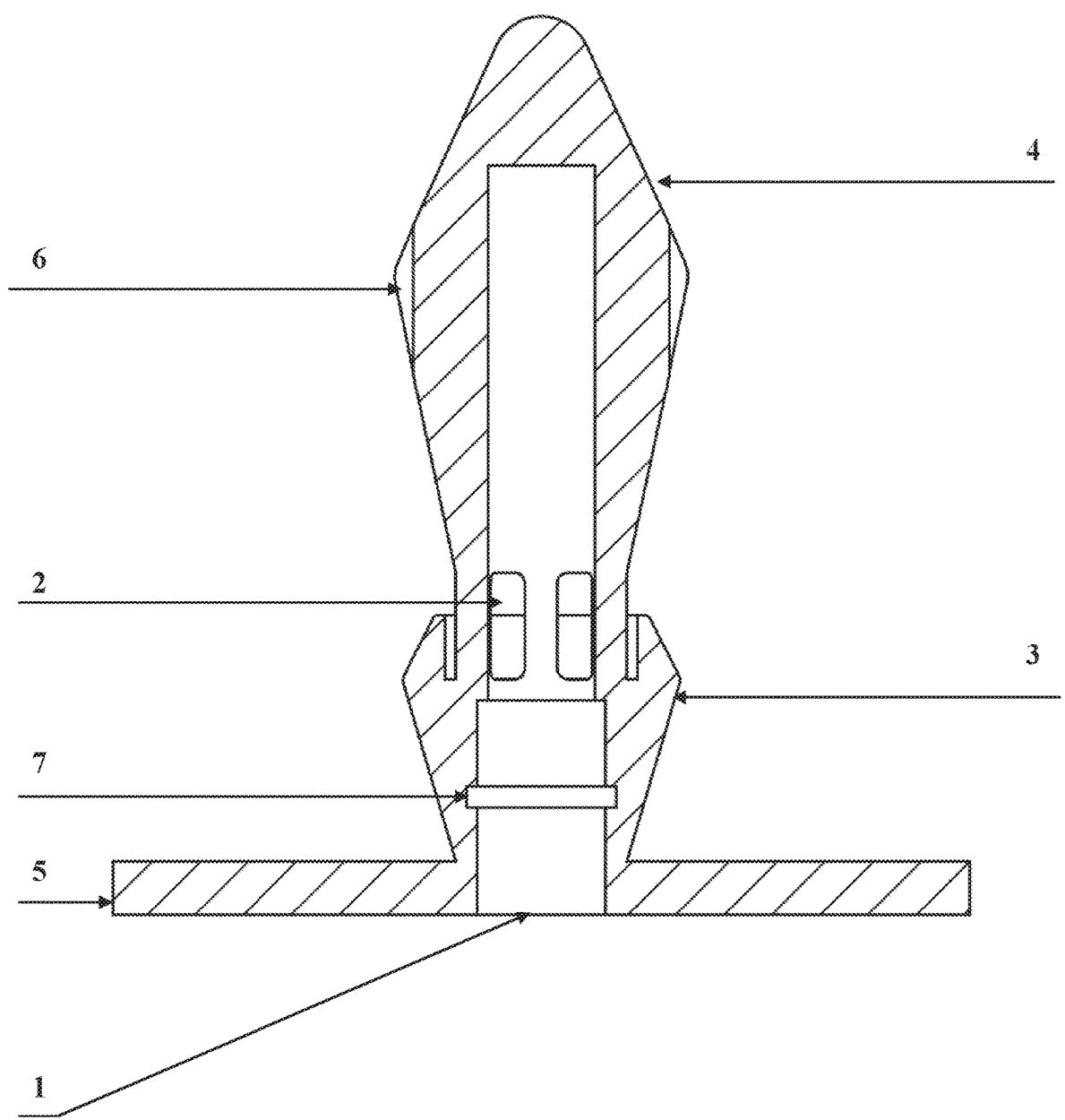
FIG. 1 is a longitudinal section of a device for the removal and collection of intestinal gases.
Figure 2:
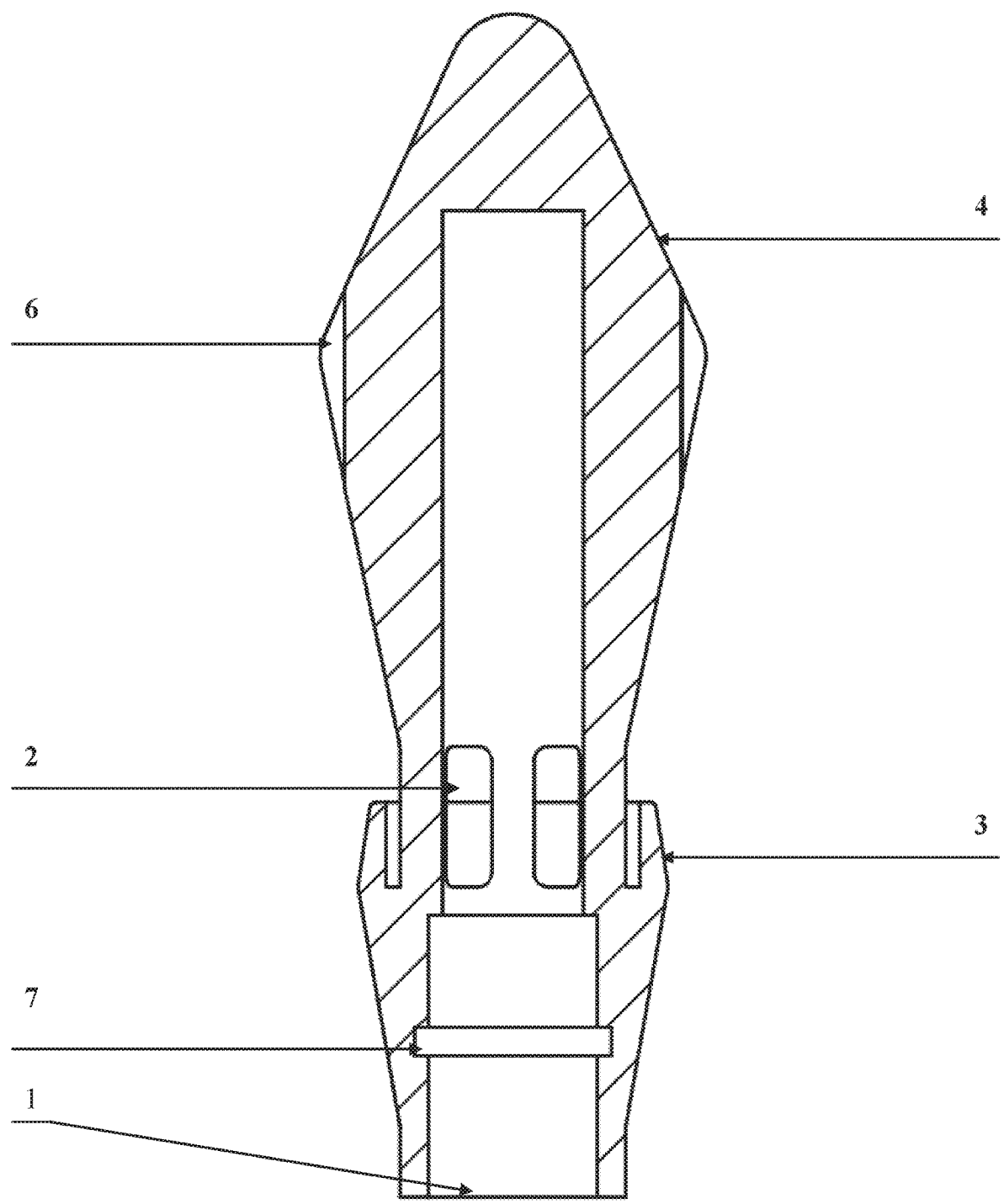
FIG. 2 is cross section of the device.
Figure 3:
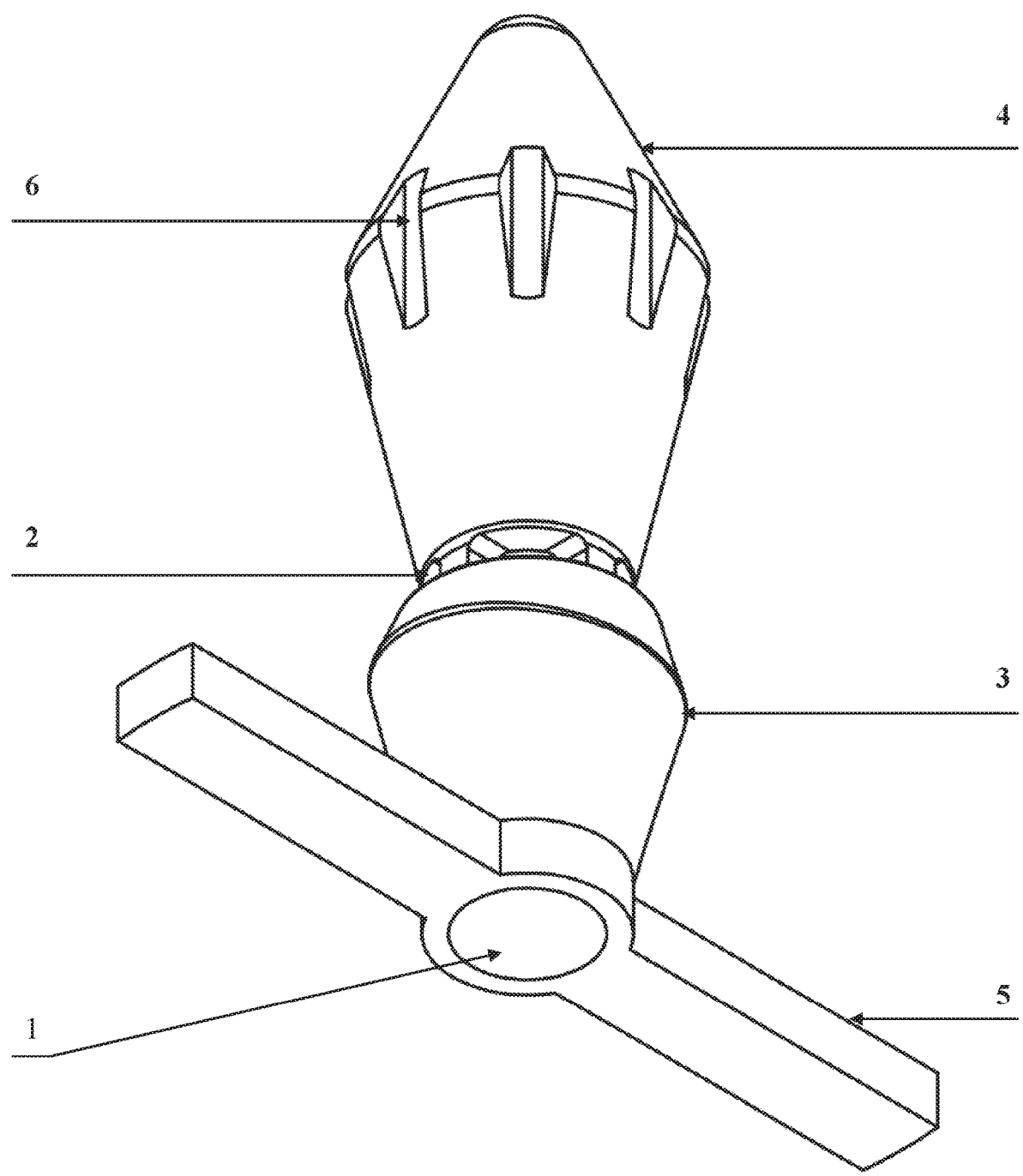
FIG. 3 is a bottom view of the device.
Figure 4:
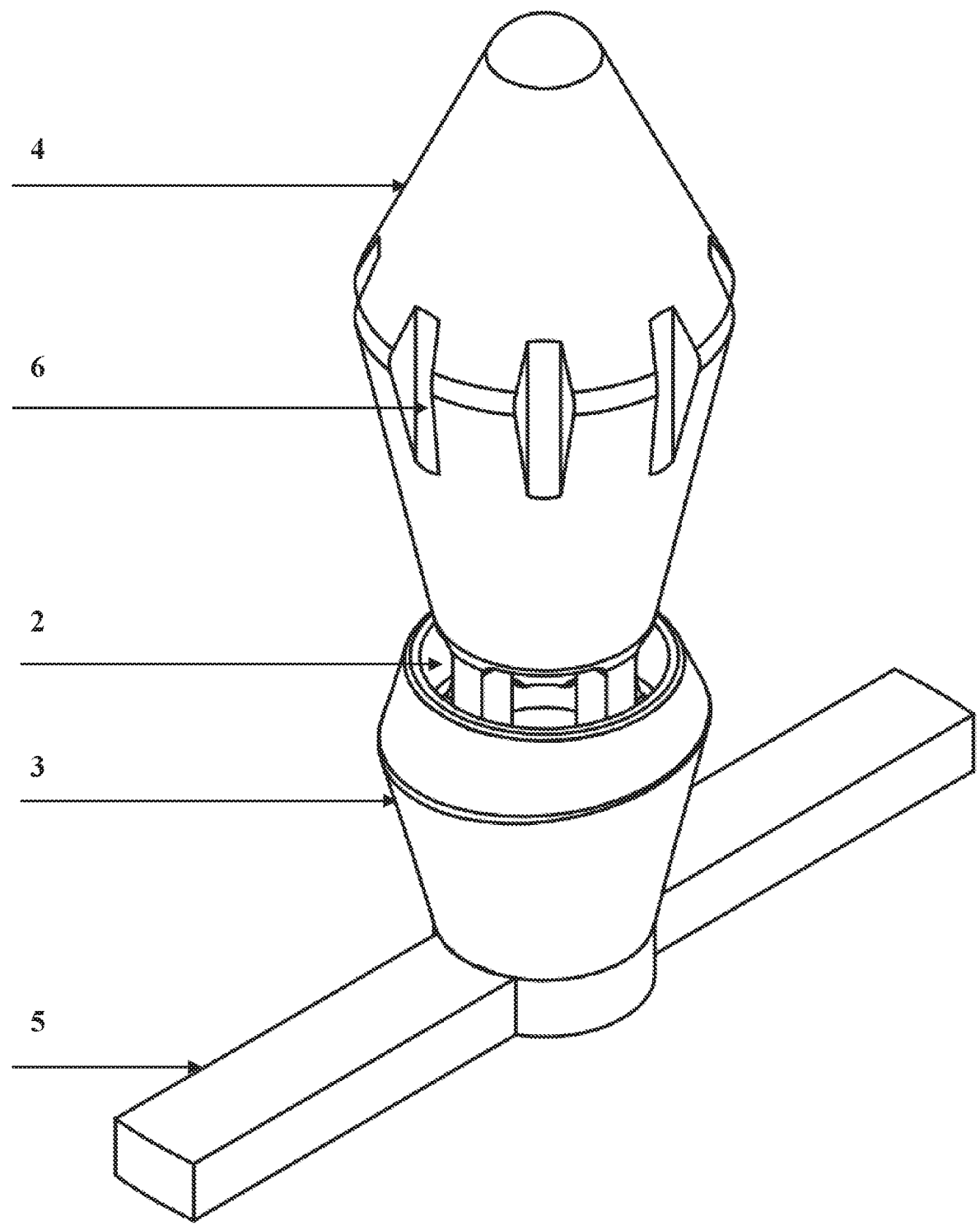
FIG. 4 is atop view of the device), where:
1—outlet;
2—window;
3—proximal protrusion;
4—distal protrusion;
5—stopper;
6—drainage grooves;
7—silencer lock groove.

In the figures, identically-acting parts are provided with the same reference numerals.

The device operates as follows: The device for removal and collection of intestinal gases consists of a housing with outlet 1, which is connected in flowing medium with window 2, which is located between protrusion 3, which is proximal relative to the hole, and distal protrusion 4. In the area of the outlet, there is stopper 5, for instance, in the form of two plates located on opposite sides of the hole, along one axis perpendicular to the hole axis. The drainage grooves 6 are located on the outside, abaxially on the distal protrusion. Inside the proximal protrusion, between the windows and the outlet, there is groove 7 of the silencer lock (not shown).

The device is inserted into the anal opening of the user, the lock is installed between the buttocks and prevents the device from penetrating into the rectum. The sphincter muscles encompass the proximal and distal protrusions. The user can partially control the compression of the sphincter muscles and regulate flatulence, and the gas flow passing from the rectum through drainage grooves 6, through window 2, into outlet 1.

The device allows for the installation of a silencer—a device that creates sound effects, —as well as a vent tube, on the other end of which a gas collector can be installed, which will further increase the comfort of the user and others.

The technical result—increased functionality, mobility and, accordingly, expanded application possibilities—is achieved due to the possibility of constant wearing the device and the absence of the need for specialist help during its installation and utilisation. The technical result—increased user comfort—is achieved by improving the quality of life due to better control of flatulence, lower sound intensity during flatulence, which leads to fewer nutritional restrictions. The user can consume food that causes increased intestinal gas production and feel more confident in critical situations, including cases of flatulence and the situations that provoke the release of gases from the intestines, for example, during a flight with lower atmospheric pressure in the aircraft cabin. The technical result—increased comfort of others—is achieved by improving the controllability, reducing the intensity of the sound during flatulence, both during normal functioning of the gastrointestinal tract and during flatulence. There is a possibility to connect a gas collector to the device, which will further increase the comfort of those around the user.

Industrial applicability. The claimed design and technical solution can be successfully used for the manufacture of rectally installed devices to remove and collect intestinal gases.

The invention claimed is:

1. A device for the removal and collection of intestinal gases by a user in the need thereof, the device comprising:
   a hollow elongated housing;
   a window on a side wall of the housing;
   an outlet located at a proximal end of the housing, the outlet is configured to be connected with the window, wherein the proximal end is defined by being proximal relative to the outlet and a distal end is defined as being distal relative to the outlet;
   a proximal collar protrusion and a distal collar protrusion, the proximal collar protrusion and the distal collar protrusion are vertically arranged on an outer surface of the housing;
   a plurality of drainage grooves arranged on an outer side of the distal collar protrusion and configured to allow intestinal gases flow; and
   a stopper configured at the outlet, the stopper is in a form of two plates located on opposite sides and being proximal to the outlet;
   wherein the window is positioned between the proximal collar protrusion and the distal collar protrusion,
   wherein the proximal collar protrusion and the distal collar protrusion are configured to be encompassed by sphincter muscles of the user, and
   wherein the device is configured to allow intestinal gases to flow through the plurality of drainage grooves, the window, and the outlet.

2. The device according to claim 1, wherein each collar protrusion is confined by two conical surfaces with adjacent bases, and the distal collar protrusion has oval bases in a cross-section.

3. The device according to claim 1, wherein the window consists of a plurality of inlet openings configured circumferentially between the collar protrusions.

4. The device according to claim 1, wherein there is a silencer or a device for creating various sounds inside the housing.

5. The device according to claim 1, further comprising a locking connection with a ring for attaching a tube for removal and/or collection of gases inside the housing.

* * * * *